United States Patent
Heimbrock et al.

[19]

[11] Patent Number: 5,996,149
[45] Date of Patent: Dec. 7, 1999

[54] TRAUMA STRETCHER APPARATUS

[75] Inventors: Richard H. Heimbrock, Cincinnati, Ohio; Charles A. Howell, Batesville, Ind.

[73] Assignee: Hill-Rom, Inc., Batesville, Ind.

[21] Appl. No.: 08/895,847

[22] Filed: Jul. 17, 1997

[51] Int. Cl.$^6$ .............................. A61G 1/00; G03B 42/02
[52] U.S. Cl. ................................. 5/601; 378/177; 378/209
[58] Field of Search ..................................... 378/177, 178, 378/179, 181, 182, 208, 209; 5/601

[56] References Cited

U.S. PATENT DOCUMENTS

| | | |
|---|---|---|
| 1,768,769 | 7/1930 | Kelley . |
| 2,989,634 | 6/1961 | Ould et al. ............................... 378/177 |
| 3,774,045 | 11/1973 | Trott . |
| 3,795,815 | 3/1974 | Weinstock et al. . |
| 3,904,531 | 9/1975 | Barrett et al. ......................... 378/177 X |
| 3,968,374 | 7/1976 | Schroeder ............................... 378/181 |
| 4,193,148 | 3/1980 | Rush . |
| 4,464,780 | 8/1984 | Ruiz . |
| 4,584,989 | 4/1986 | Stith . |
| 4,651,364 | 3/1987 | Hayton et al. . |
| 4,893,323 | 1/1990 | Cook, III . |
| 4,905,266 | 2/1990 | Kuck et al. . |
| 4,916,725 | 4/1990 | Quinter et al. . |
| 4,926,457 | 5/1990 | Poehner et al. . |
| 4,947,418 | 8/1990 | Barr et al. . |
| 5,016,268 | 5/1991 | Lotman . |
| 5,138,646 | 8/1992 | Hubert et al. . |
| 5,155,758 | 10/1992 | Vogl . |
| 5,255,303 | 10/1993 | DiMaio et al. . |
| 5,422,928 | 6/1995 | Payne . |
| 5,575,026 | 11/1996 | Way et al. . |
| 5,703,925 | 12/1997 | Wright . |

FOREIGN PATENT DOCUMENTS

| | | |
|---|---|---|
| 2534704 | 4/1984 | France . |
| 43 44 123 A1 | 6/1995 | Germany . |
| 1 200 814 | 8/1970 | United Kingdom . |

OTHER PUBLICATIONS

"ED II Emergency Department Stretcher", Stryker Medical Division product brochure, two pages, date unknown.
"921 InstaCare Trauma/Emergency Stretcher Modifications", Stryker Medical brochure, two pages, date unknown.
"Beta One X–Ray Bed", Beta Medical Products, Inc. brochure, two pages, date unknown.
"X–ray Trauma Stretcher", Beta Medical Products, Inc. brochure, two pages, date unknown.
"Patient Handling Systems", Stryker Medical Division brochure, two pages, date unknown.
"InstaCare/Emergency Stretcher Model 1000E", Stryker Medical brochure, two pages, date unknown.
"Advantage Series Trauma Stretcher Model 1002", Stryker Patient Handling brochure, three pages, Sep., 1993.
"Full Length X–Ray Trauma Stretcher Model 1020 Renaissance Series", Stryker Medical brochure, two pages, May, 1995.
"The Gemini Series", Hausted brochure, two pages, date unknown.
"Hausted Specialty Stretchers, The Unicare Series", Hausted product brochure, two pages, date unknown.
"Colson Trauma Stretcher", Colson brochure, one page, date unknown.
"530 ED/Trauma Stretcher", Midmark Corporation brochure, six pages, 1989.
"The Midmark 550/555 Stretcher", Midmark Corporation brochure, four pages, 1995.
"Here are just a few of the ways a C–100 cassette holder from Monee X–Ray Works can help you!", Monee X–Ray Works brochure, four pages, date unknown.
"Dual Control Critical Care Bed Model 2020", Stryker Medical brochure, two pages, date unknown.

*Primary Examiner*—Michael F. Trettel

[57] ABSTRACT

A bed includes a frame, a patient support deck coupled to the frame, and an x-ray tray located below the deck. The x-ray tray is configured to receive an x-ray cassette. The bed also includes a lifting mechanism located between the frame and the x-ray tray to move the x-ray tray from a lower first position spaced apart from the deck to permit loading of the x-ray cassette on the x-ray tray and an elevated second position located closer to the deck.

34 Claims, 11 Drawing Sheets

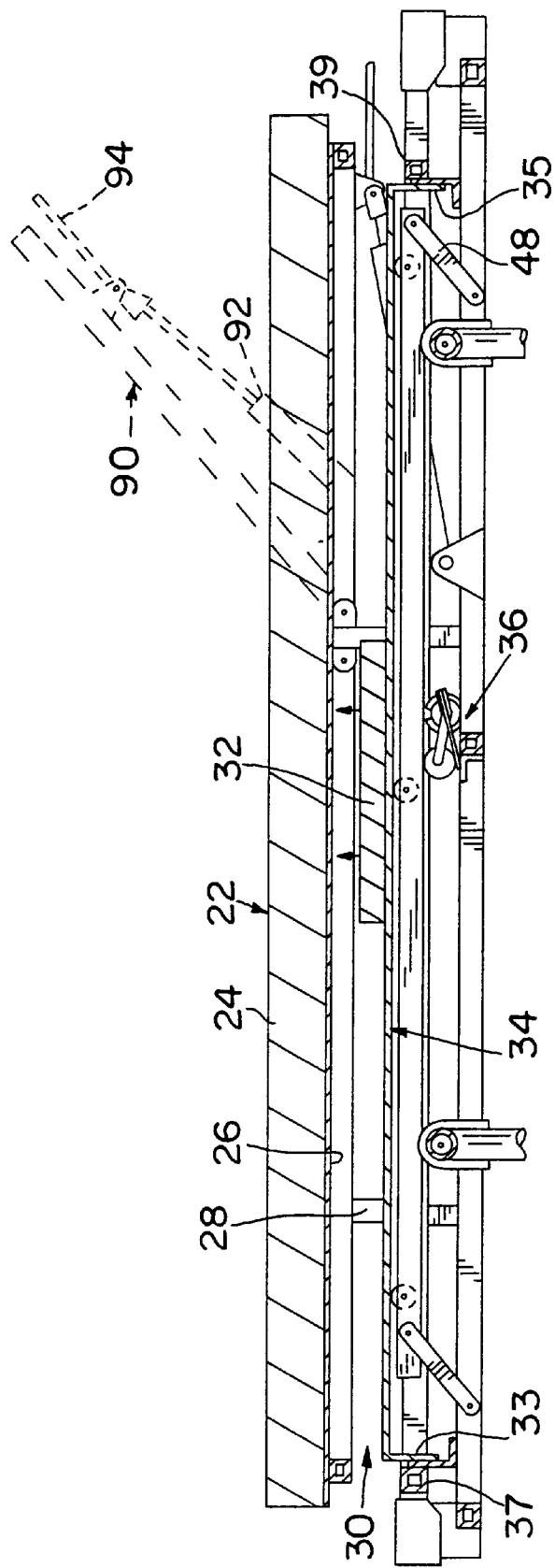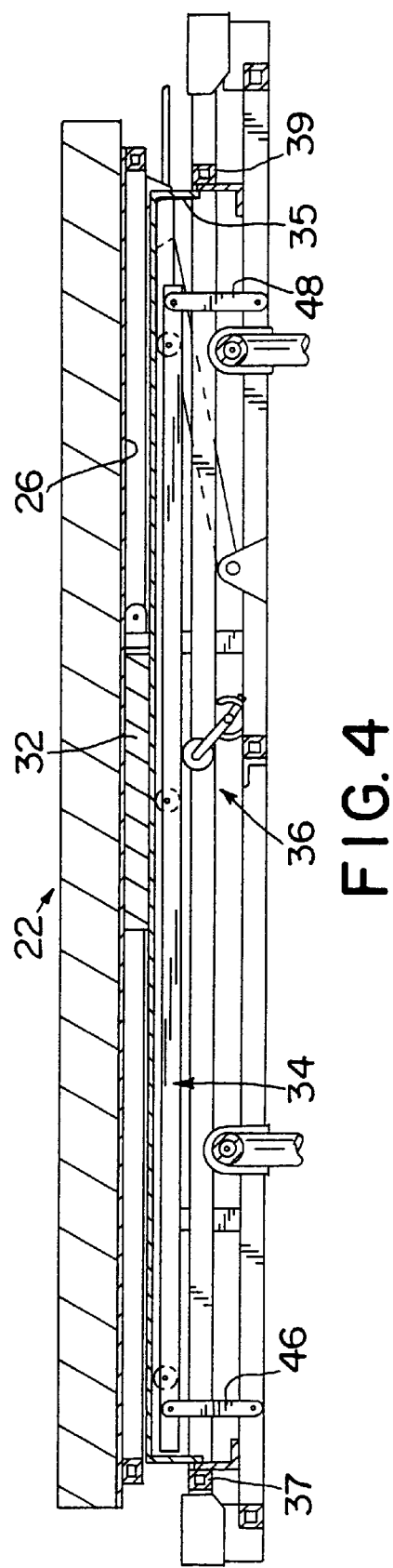
FIG. 3
FIG. 4

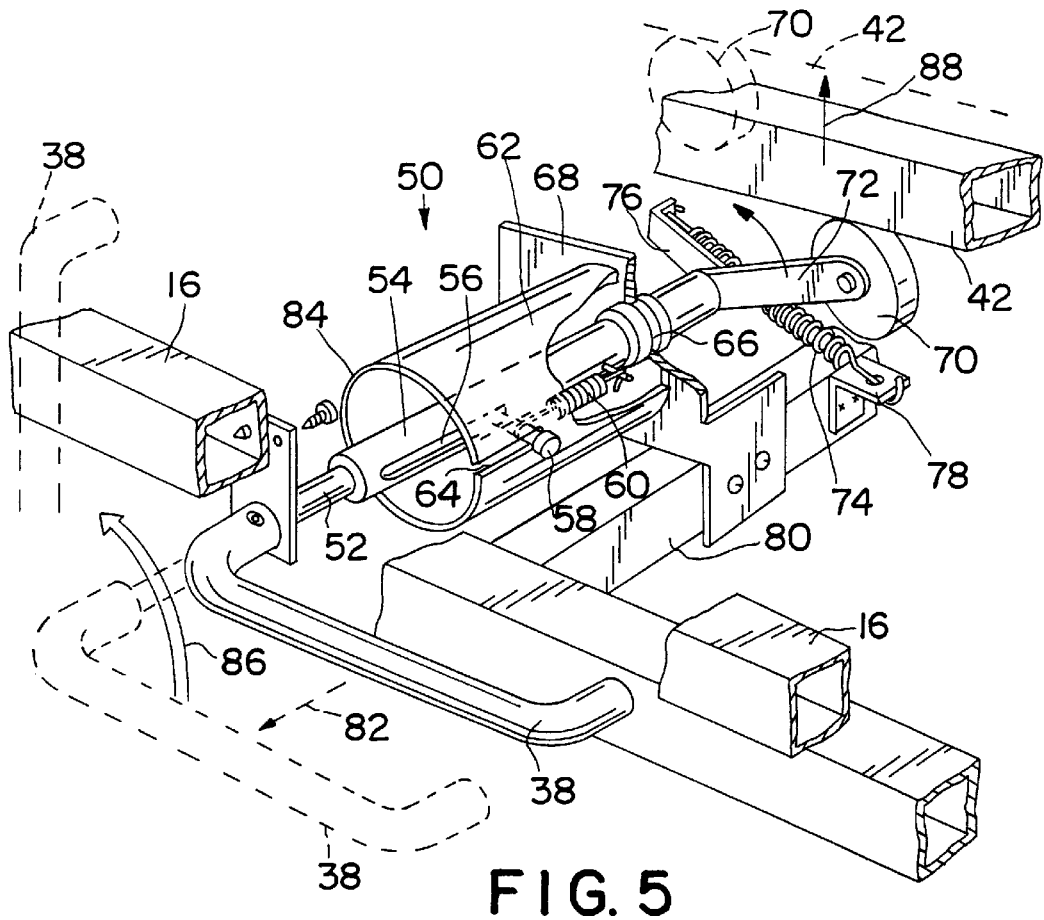
FIG. 5
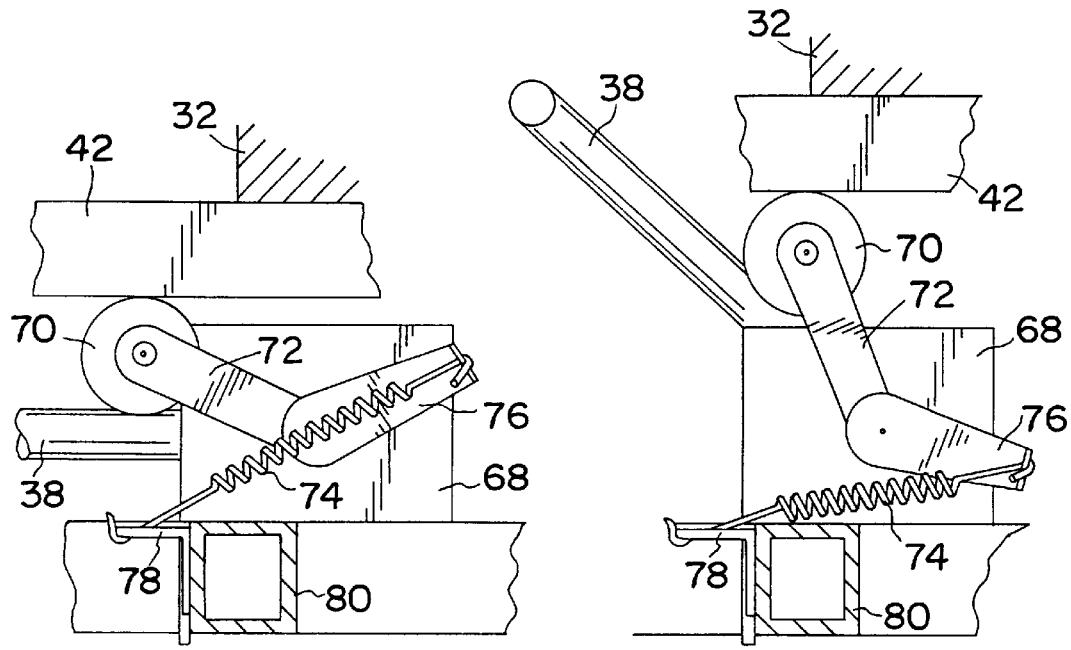
FIG. 6
FIG. 7

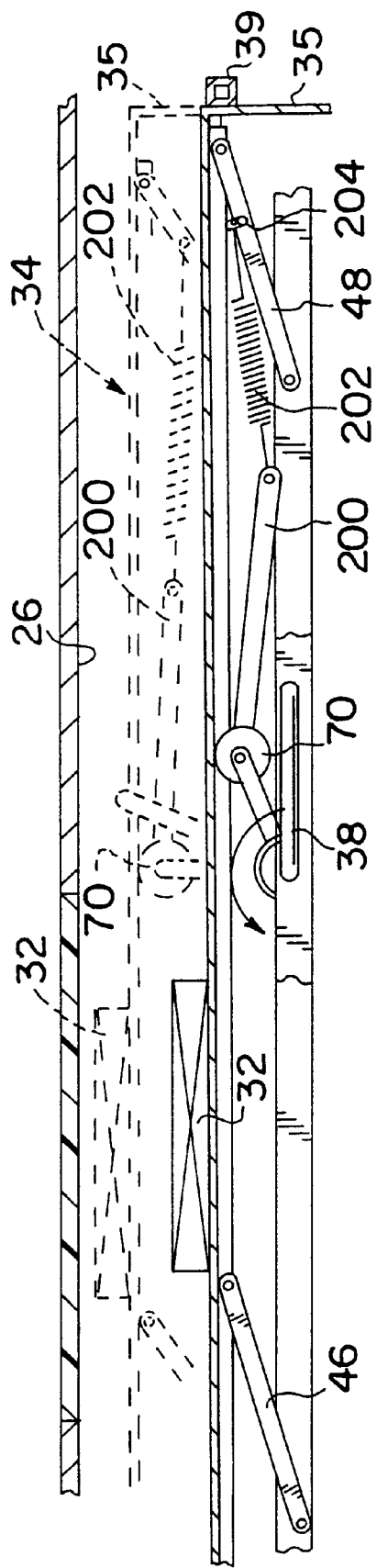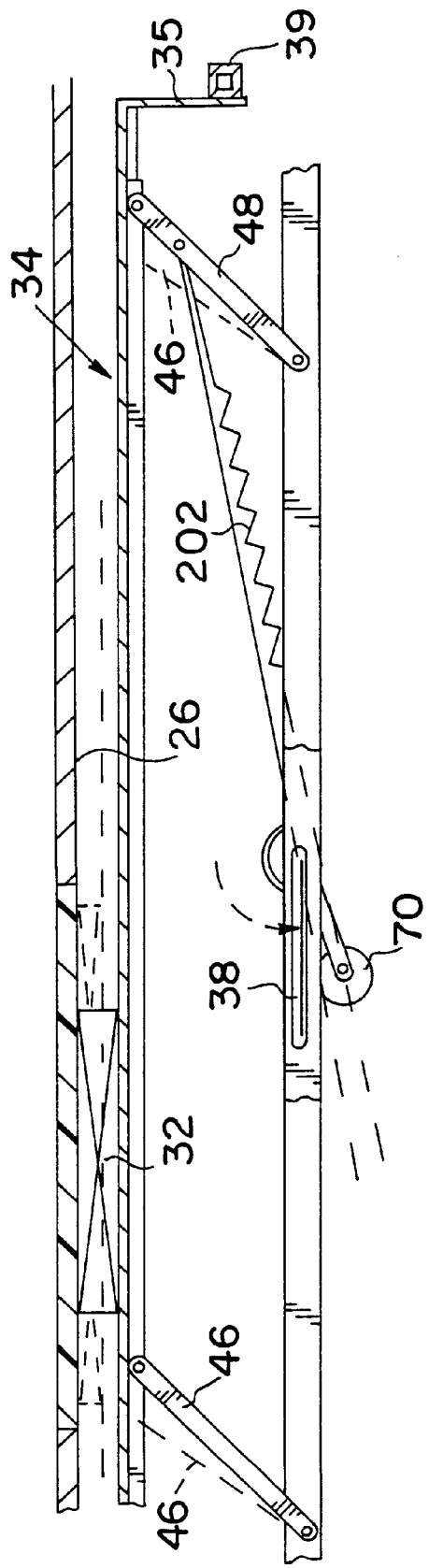

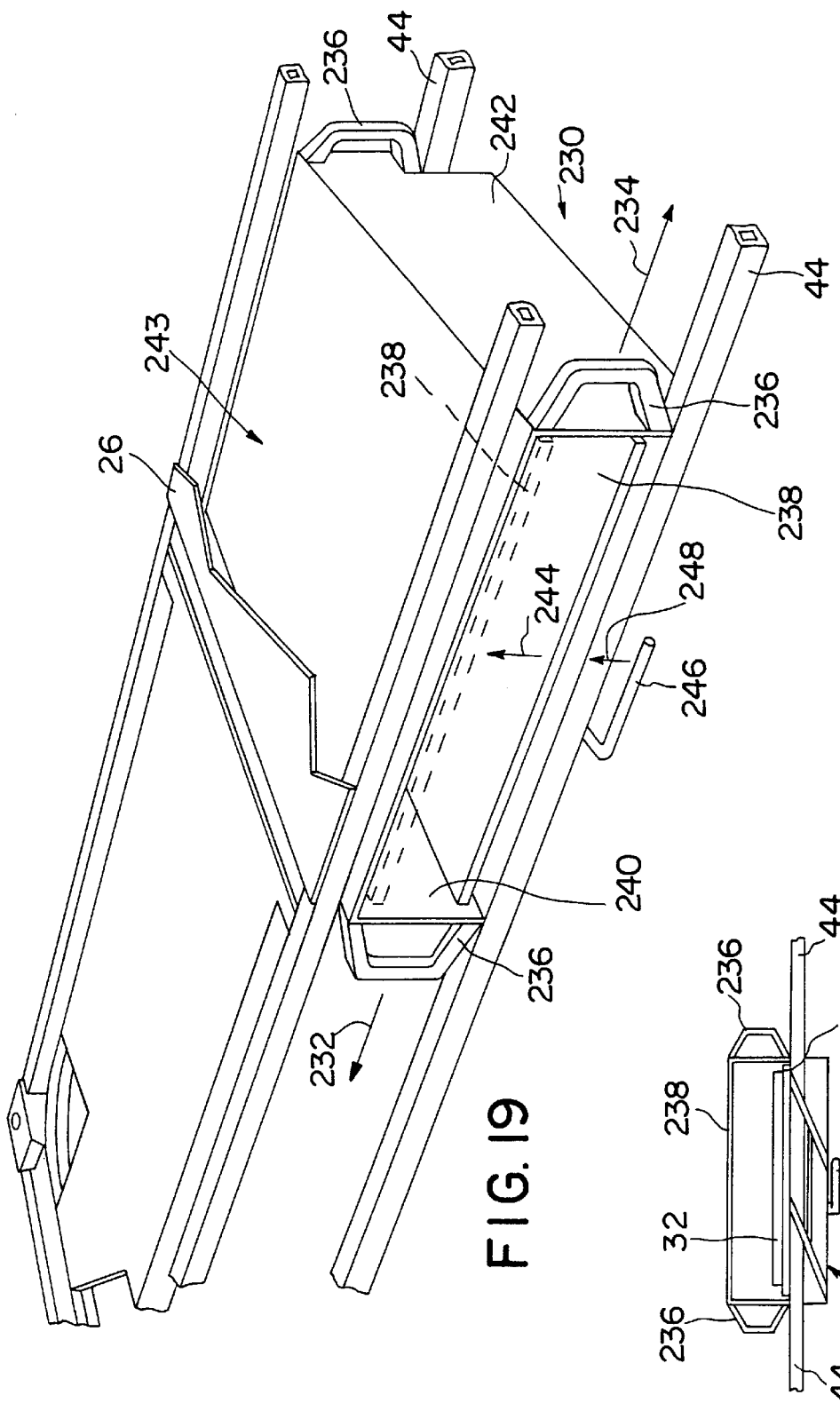

TRAUMA STRETCHER APPARATUS

BACKGROUND AND SUMMARY OF THE INVENTION

The present invention relates to a stretcher or hospital bed. More particularly, the present invention relates to a stretcher which facilitates taking x-rays of a patient located on a support surface of the stretcher.

Although the term "stretcher" is used throughout the specification of the present application, it is understood that the novel features of the invention may be incorporated into any type of bed or patient support device.

Stretchers or beds which include structures for holding an x-ray cassette are known. See, for example, U.S. Pat. Nos. 1,768,769; 3,774,045; 4,193,148; 4,584,989; 4,651,364; 4,893,323; 4,905,266; 4,916,725; 4,926,457; 4,947,418; 5,155,758; 5,255,303; and 5,422,928.

During an emergency or trauma situation, it is important to have the maximum flexibility in placement of an x-ray cassette relative to a patient. In addition, it is important to provide the best x-ray image possible on the x-ray cassette. Typically, x-ray radiation spreads out or magnifies as the distance increases between the patient and the x-ray cassette. Therefore, it is desirable to place the x-ray cassette as close to the patient as possible.

The present invention provides an improved x-ray cassette support tray located adjacent a patient support surface of the stretcher. The improved x-ray tray permits the x-ray cassette to be loaded at substantially any horizontal location below the patient support surface by sliding the cassette onto the tray using the hands. Enough room is provided between the frame and the patient support surface for hands to pass between. After the x-ray cassette is loaded on the x-ray tray at a desired horizontal location below the patient, the x-ray tray can then be lifted upwardly by a lifting mechanism to position the x-ray cassette adjacent a bottom of the patient support surface to improve x-ray imaging on the cassette.

According to one aspect of the present invention, a bed includes a frame and a patient support deck coupled to the frame. The deck has a bottom surface. The bed also includes an x-ray tray located below the deck. The x-ray tray is configured to receive an x-ray cassette. The bed further includes a lifting mechanism located between the frame and the x-ray tray to move the x-ray tray from a lower first position spaced apart from the deck to permit loading of the x-ray cassette on the x-ray tray and an elevated second position located closer to the deck.

In the illustrated embodiment, the x-ray tray moves only vertically relative to the frame between the lower first position and the elevated second position. The illustrated lifting mechanism includes a linkage which slides relative to the x-ray tray so that the x-ray tray moves upwardly without horizontal movement relative to the frame. The x-ray tray includes flanges at opposite ends which are configured to engage first and second cross members of the frame to hold the x-ray tray in the same horizontal position relative to the frame during movement of the x-ray tray. It is understood that the lifting mechanism may be manually or automatically powered and may lift the x-ray tray straight up without sliding relative to the x-ray tray.

In the illustrated bed, the deck has a length dimension and a width dimension, and the x-ray tray extends below substantially the entire deck. The x-ray tray includes an upper x-ray cassette supporting surface and the lifting mechanism includes a parallelogram linkage coupled to the frame. The x-ray tray may include a non-slip top surface for engaging the x-ray cassette.

In one embodiment, the lifting mechanism includes a handle pivotably coupled to the frame and a wheel coupled to the handle. The wheel is configured to engage the x-ray tray and move the x-ray tray upwardly to its second elevated position when the handle is rotated relative to the frame. The handle is movable to a storage position located under the frame. The illustrated handle is spring-biased to the storage position.

In another illustrated embodiment, the lifting mechanism includes a handle pivotably coupled to the frame and a spring having a first end coupled to the handle. A second end of the spring is coupled to a linkage of the lifting mechanism to lift the linkage and move the x-ray tray upwardly to its second elevated position when the handle is rotated relative to the frame. In another illustrated embodiment, the x-ray tray and the lifting mechanism are slidable on the frame below the patient support deck.

According to another aspect of the present invention, a holder apparatus is provided for retaining an x-ray cassette against a bottom surface of a patient support deck of a bed on a back section having an outer frame with first and second side frame members adjacent the patient support deck. The holder apparatus includes a cassette channel member configured to receive an end of the x-ray cassette. The channel member is pivotably coupled to the first side frame member, and the channel member being pivotable from a storage position aligned generally parallel to the first side frame member to a second x-ray position extending over the bottom surface of the patient support deck. The holder apparatus also includes a cassette retainer coupled to the frame. The retainer is configured to engage the x-ray cassette and hold the x-ray cassette against the bottom surface of the deck.

The illustrated channel member is slidably mounted to the frame and may be spring-biased toward its storage position. The channel member is configured to engage the first side frame member when the channel member is in its x-ray position to hold the channel member generally perpendicular to the first side frame member. The illustrated retainer is a spring arm pivotably coupled to the second side frame member. The spring arm is pivotable from a storage position aligned generally parallel to the second side frame member and in x-ray position located over the deck.

According to yet another embodiment of the present invention, a bed includes a frame, and a patient support deck coupled to the frame. The deck has a bottom surface and a head section movable to an upwardly pivoted position relative to the frame. The bed also includes an x-ray tray located below the deck. The x-ray tray is formed to include a recessed portion. The bed further includes an x-ray cassette holder pivotably coupled to the x-ray tray and movable from a storage position located inside the recessed portion of the x-ray tray to an x-ray position to hold an x-ray cassette against the head section of the deck when the head section is located in its upwardly pivoted position.

In the illustrated embodiment, the cassette holder includes a first member pivotably coupled to the x-ray tray, a second member slidably coupled to the first member and movable from a retracted position to an extended position, and a channel member coupled to the second member, the channel member being configured to hold an end of the x-ray cassette against the head section of the deck when the cassette holder is in its x-ray position. A second channel member is coupled to the frame of the bed to hold another end of the x-ray cassette. A locking mechanism is provided to secure the first and second members together in a desired position.

According to still another aspect of the present invention, an x-ray cassette holder is configured to be coupled to a frame of a bed. The cassette holder includes first, second, and third telescoping members, and a mounting mechanism coupled to the first telescoping member. The mounting mechanism is configured to engage the frame of the bed in two orientations. The cassette holder also includes a first cassette channel coupled to the second telescoping member, a second cassette channel coupled to the third telescoping member, a first locking member which couples the first telescoping member to the second telescoping member, and a second locking member which couples the second telescoping member to the third telescoping member.

According to a further aspect of the present invention, an x-ray cassette holder is configured to be coupled to a frame of a bed having a patient support surface. The cassette holder apparatus includes a support member, and a mounting mechanism coupled to the support member. The mounting mechanism is configured to engage the frame of the bed. The cassette holder also includes an arm having first and second ends. The first end of the arm is pivotably coupled to the support member. The cassette holder further includes a cassette channel pivotably coupled to the second end of the arm for movement over the support surface of the bed. The channel is configured to receive an end of an x-ray cassette to hold the x-ray cassette adjacent a patient on the patient support surface. In the illustrated embodiment, the support includes at least two telescoping sections to adjust the height of the channel relative to the patient support surface of the bed.

According to an additional aspect of the present invention, an x-ray cassette holder is configured to be coupled to a frame of a bed. The cassette holder includes first and second telescoping members, and a mounting mechanism coupled to the first telescoping member. The mounting mechanism is configured to engage the frame of the bed. The cassette holder also includes a first cassette channel coupled to the first telescoping member, and a second cassette channel coupled to the second telescoping member. The first and second telescoping members are movable relative to each other to hold an x-ray cassette between the first and second cassette channels. The cassette holder further includes an extension rod connecting the first telescoping member to the second telescoping member to permit movement of the first telescoping member relative to the second telescoping member while preventing separation of the first telescoping member from the second telescoping member.

In the illustrated embodiment, the mounting mechanism includes a channel configured to engage the frame and a coupler configured to secure the mounting mechanism to the first telescoping member. The extension rod extends into an interior region of both the first and second telescoping members. The extension rod has washers coupled to opposite ends. A first pin is coupled to the first telescoping member, and a second pin is coupled to the second telescoping member. The first and second pins are configured to cooperate with the first and second washers to retain the extension rod within the first and second telescoping members.

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which:

FIG. 3 is a sectional view taken along lines 3—3 of FIG. 1 illustrating a patient support surface and the x-ray tray and lifting mechanism with the x-ray tray in its lowered position for receiving a x-ray cassette;

FIG. 4 is a sectional view similar to the FIG. 3 illustrating the x-ray tray moved to its upwardly extended x-ray position so that the x-ray cassette is located against a bottom surface of the patient support surface;

FIG. 5 is a perspective view illustrating the lifting mechanism of FIGS. 2–4;

FIG. 6 is a partial sectional view further illustrating the lifting mechanism of FIG. 5 when the x-ray tray is in its lowered position;

FIG. 7 is a sectional view similar to FIG. 6 illustrating the lifting mechanism moving the x-ray tray toward its elevated position;

FIG. 16 is a sectional view of the lifting mechanism of FIG. 15 illustrating movement of the lifting mechanism to lift the x-ray tray from its lowered position to an intermediate position;

FIG. 17 is a sectional view similar to FIG. 16 illustrating further movement of the lifting mechanism to raise the x-ray tray to its elevated position so that the x-ray cassette is located against a bottom of the patient support surface;

FIG. 19 is a perspective view illustrating a further embodiment of the lifting mechanism which includes a movable tray mounted below the deck of the bed which can slide relative to the deck to position an x-ray cassette at a desired location beneath a patient support deck;

FIG. 20 is a side elevation view of the lifting mechanism of FIG. 19; and

DETAILED DESCRIPTION OF THE DRAWINGS

Figure 1:
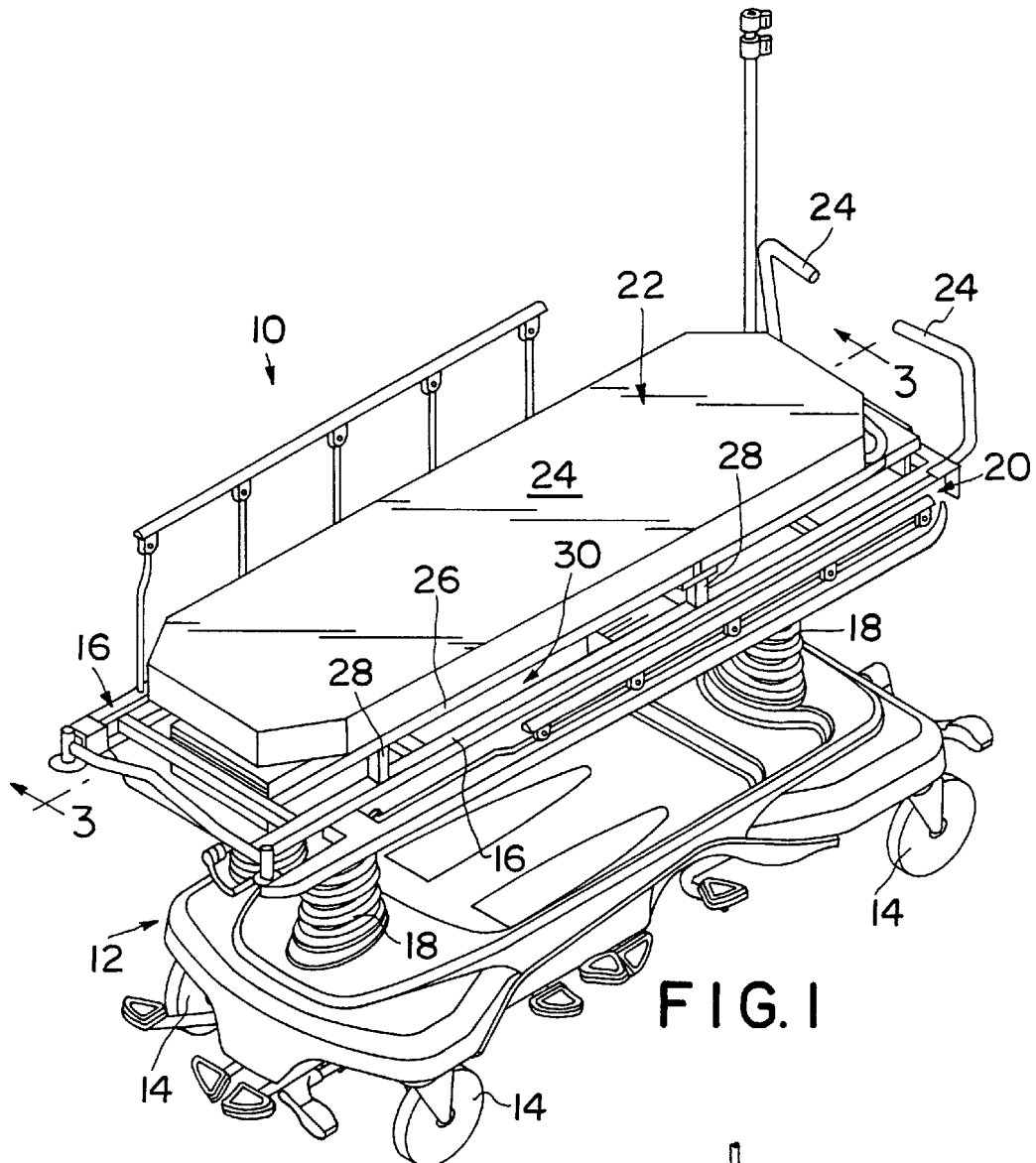
FIG. 1 is a perspective view of a trauma stretcher apparatus of the present invention.

Referring now to the drawings, FIG. 1 illustrates a stretcher apparatus 10 of the present invention. The stretcher 10 includes a base 12 having casters 14 and a frame 16 coupled to the base 12 by front and rear lifting mechanisms 18. A pair of side rails 20 are located on opposite sides of a patient support surface 22. Push handles 24 are located adjacent a head end of stretcher 10.

Although a stretcher 10 is illustrated in connection with the present invention, it is understood that any type of bed or patient support surface may be used in accordance with the present invention. In other words, the features of the present invention are not limited to use with a stretcher.

The patient support surface 22 of the present invention includes a mattress 24 which may be any type of mattress structure. A support deck 26 is spaced apart from frame 16 by standoffs 28 to provide a space 30 for receiving an x-ray cassette 32 as best illustrated in FIGS. 3 and 4. The x-ray cassette 32 can be loaded at any desired position beneath the patient support surface 22. The x-ray cassette 32 rests on an x-ray tray 34 movable between a lowered cassette loading position illustrated in FIG. 3 and an elevated x-ray position to move the cassette 32 into engagement with a bottom of patient support deck 26.

A pair of lifting mechanisms 36 each include a handle actuator 38 on opposite sides of the stretcher 10. X-ray tray 34 rests on a parallelogram linkage 40 which moves the x-ray tray 34 from its lowered position illustrated in FIG. 3 to its elevated position illustrated in FIG. 4. X-ray tray 34 includes opposite end flanges 33 and 35 located between cross bars 37 and 39 of frame 16 to maintain the tray in the same horizontal position relative to support deck 26 as the x-ray tray 34 moves up and down. By moving the x-ray cassette 32 to the elevated position adjacent the bottom surface of support deck 26, images on the x-ray cassette 32 are clearer. The x-ray tray 34 is centered on the stretcher 10 and extends substantially the entire length and width of patient support surface 22. This facilitates placement of the x-ray cassette 32 at any desired location. Top surface 40 of x-ray tray 34 is covered with a non-slip pad having texture to prevent sliding of the x-ray cassette 32 when the stretcher is in a Trendelenburg or reverse Trendelenburg position. Parallelogram linkage 40 includes upper horizontal members 42, lower horizontal members 44, and end connectors 46 and 48. Upper members 42 slide relative to tray 34 as shown in FIGS. 3 and 4.

Figure 2:
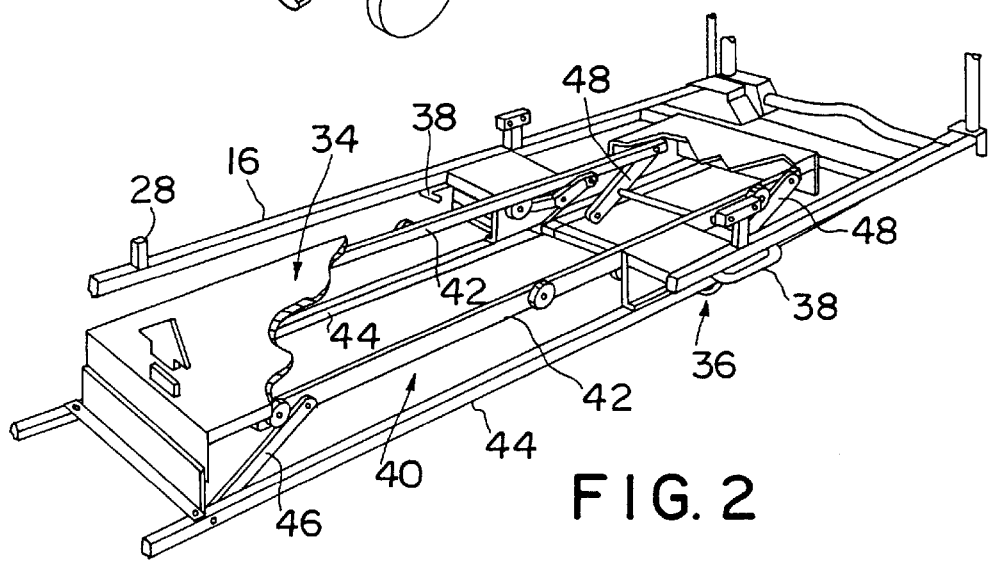
FIG. 2 is a perspective view of an x-ray tray and lifting mechanism according to one embodiment of the present invention.

Further details of the lifting mechanism 36 of FIGS. 2–3 are illustrated in FIG. 5–7. Lifting mechanisms 36 located on opposite sides of the stretcher 10 work in identical manners. Handle 38 is attached to rod 52 which extends into a sleeve 54 having a slot 56. A pin 58 is coupled to rod 52 of handle 38. Pin 58 is coupled to spring 60 to bias the handle 38 inwardly to a storage position located below frame member 16 as illustrated in solid lines in FIG. 5. An outer tube 62 surrounds sleeve 54. Outer tube 62 includes a slot 64 for receiving pin 58. Sleeve 54 includes a bearing 66 coupled to wall 68. A roller 70 is coupled to an end of sleeve 54 by arm 72. A spring 74 is coupled to an arm 76 which is also coupled to the distal end of sleeve 54. An opposite end of spring 74 is coupled to a bracket 78. Bracket 78 is coupled to a frame member 80 of stretcher 10.

When it is desired to move the x-ray tray 34 from its lowered position of FIG. 3 to its upwardly extended x-ray position of FIG. 4, the handle 38 is pulled outwardly to the dotted position as illustrated by arrow 82 in FIG. 5. Pin 58 moves within slot 56 of sleeve 54 and within slot 64 of outer tube 62. Once pin 58 clears the end 84 of tube 62, handle 38 can rotate in the direction of arrow 86 to the vertical position illustrated in FIG. 5. This pivotable movement of handle 38 causes rotation of rod 52, sleeve 54, arm 72, and wheel 70. Wheel 70 engages frame member 42 of x-ray tray 34 to lift the x-ray tray 34 upwardly in the direction of arrow 88 as illustrated by the dotted lines of FIG. 5.

FIGS. 6 and 7 further illustrate lifting of the x-ray tray as the handle 38 is rotated. Spring 74 pulls arm 76 to assist raising of the x-ray tray 34.

As best illustrated in FIGS. 3 and 4, the x-ray cassette 32 can be located at any desired position beneath the patient support surface 22. The x-ray tray 34 extends substantially beneath the entire patient support surface 22. When the x-ray tray 34 is moved to its upwardly extended position, the x-ray cassette 32 is placed adjacent the bottom surface of the patient support deck 26. This improves the image on the x-ray cassette 32 by reducing magnification of the x-rays. The deck 26 is illustratively made from a thick Formica, radiolucent material having the equivalent of less than one millimeter of aluminum to permit x-rays to pass through deck 26.

Figure 8:
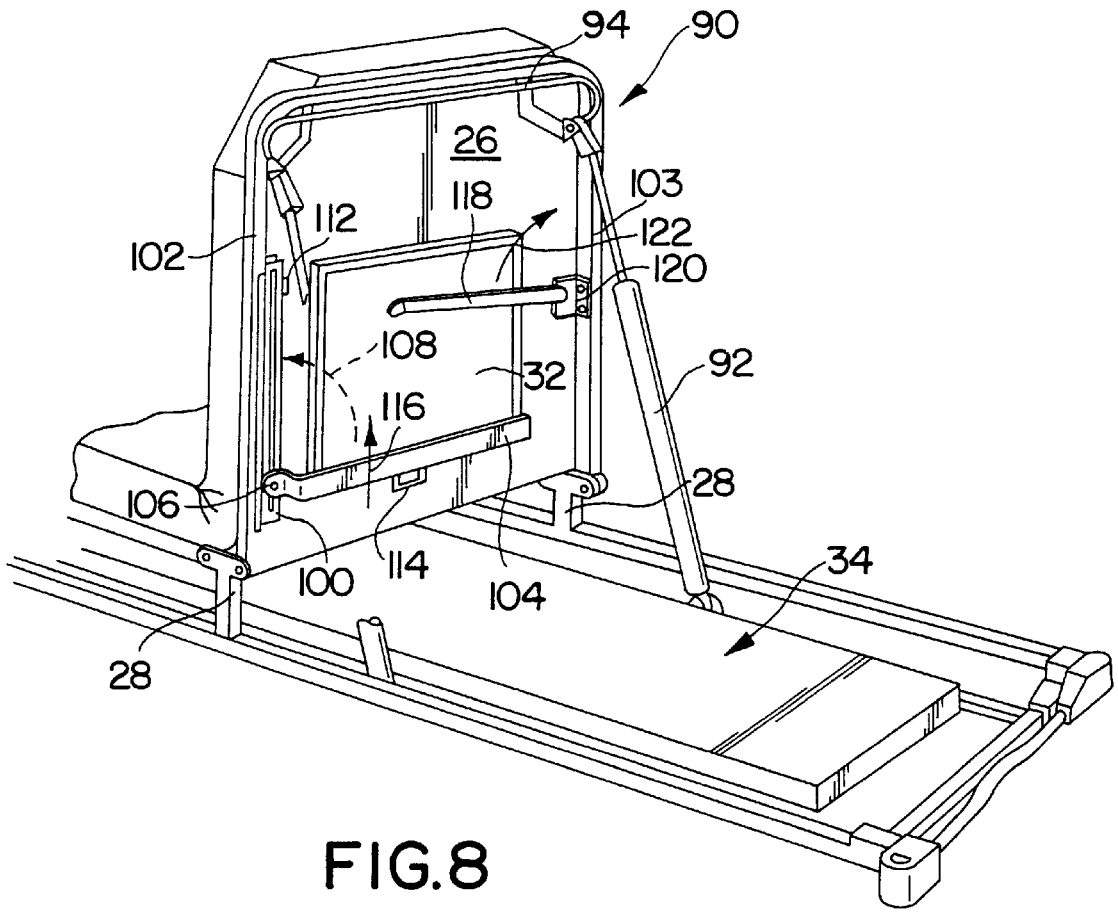
FIG. 8 is a perspective view illustrating one embodiment of a cassette holder for holding an x-ray cassette against a head section of the patient support surface when the head section is in its upwardly pivoted position.

A head section 90 of the patient support surface 22 and deck 26 is pivotable upwardly to an elevated position as illustrated in FIGS. 3 and 8. A pair of pneumatic cylinders 92 are coupled to head section 90. An actuator 94 releases the pneumatic cylinders 92 to permit movement of the head section 90. Once the actuator 94 is released, cylinders 92 hold the head section 90 at the desired angle. It is desirable to be able to take x-rays of a patient when the head section 90 is in the elevated position. Therefore, another cassette holder is required to hold the x-ray cassette 32 against a bottom surface of the deck 26 of head section 90 to provide a proper x-ray image.

Figure 9:
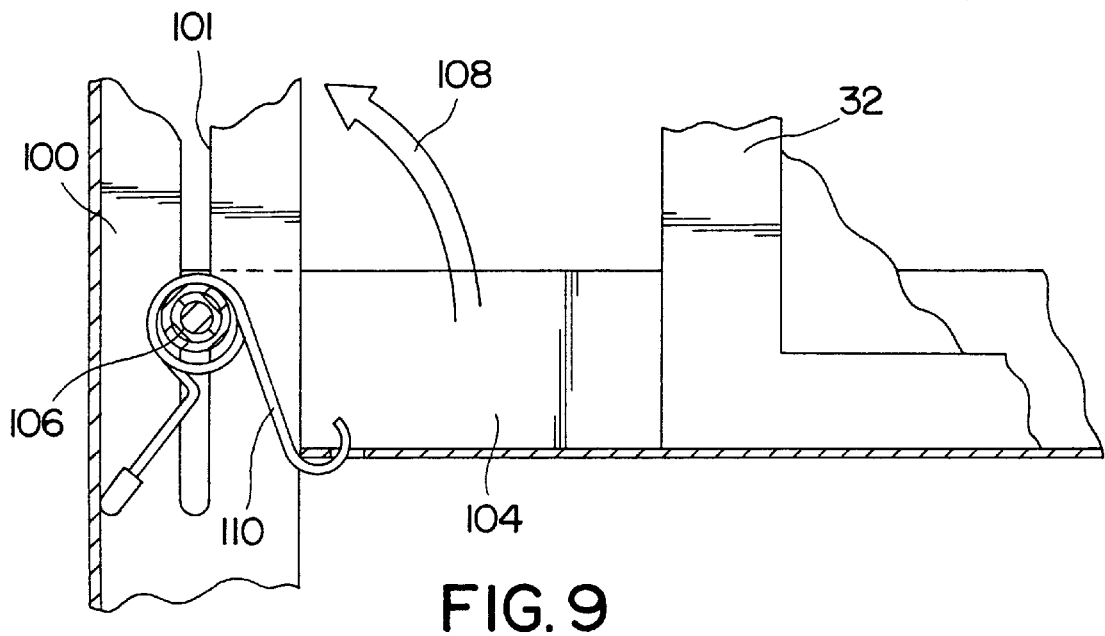
FIG. 9 is a partial sectional view illustrating further details of the x-ray cassette holder of FIG. 8.

One embodiment of an upright cassette holder is illustrated in FIGS. 8 and 9. A track 100 is coupled to a side frame member 102. A cassette holder channel 104 is pivotably coupled to track 100 by a fastener 106. As illustrated in FIG. 9, the cassette channel 104 is biased upwardly in the direction of arrow 108 by a spring 110. A retainer 112 is provided to retain the cassette holder channel 104 in its upright position adjacent and parallel to track 100 for storage. Spring 110 is not required.

When it is desired to load the cassette 32, the channel 104 is pivoted downwardly using handle 114. An end of cassette 32 is placed within channel 104 as best illustrated in FIG. 9. Channel 104 can then slide upwardly in the direction of arrow 116 to position the cassette 32 at a desired location adjacent patient support deck 26. A spring retainer arm 118 is coupled to side frame member 103 by bracket 120. Spring retainer arm 118 is pivotable upwardly in the direction of arrow 122 when not in use to lie adjacent and parallel to frame member 103. When not in use, cassette holding channel 104 is pivoted upwardly in the direction of arrow 108. Therefore, the retainer arm 118 and cassette holder 104 are not in an x-ray window below deck 26 of head section 90 when in the storage position.

Figure 10:
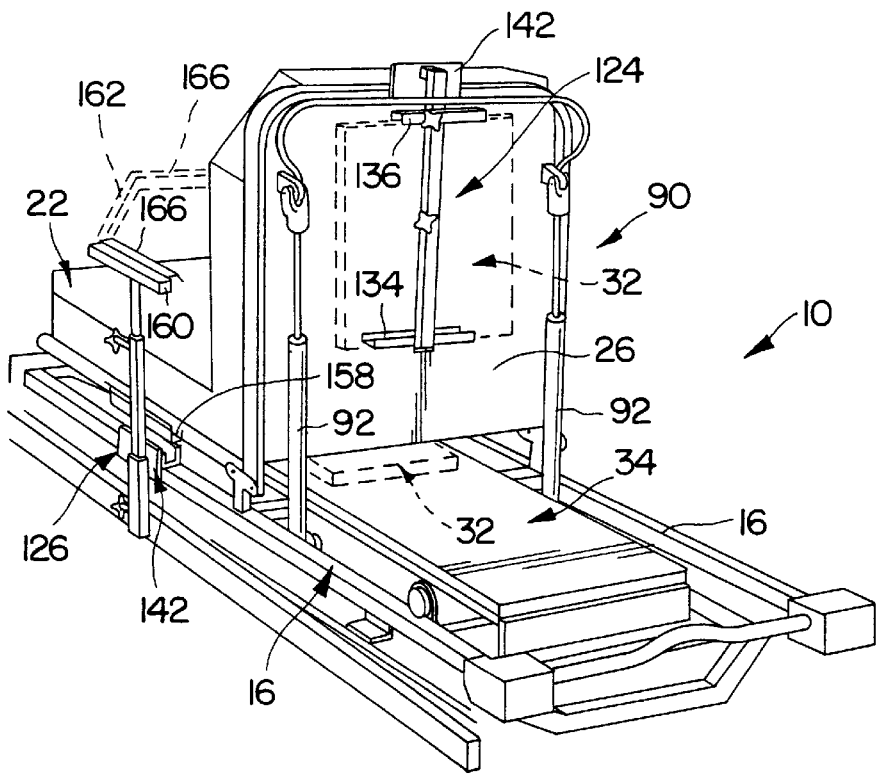
FIG. 10 is a perspective view illustrating x-ray cassette holders configured to be mounted either to a side of the bed frame adjacent the patient support surface or to the head section of the bed to support x-ray cassettes.
Figures 11, 12:
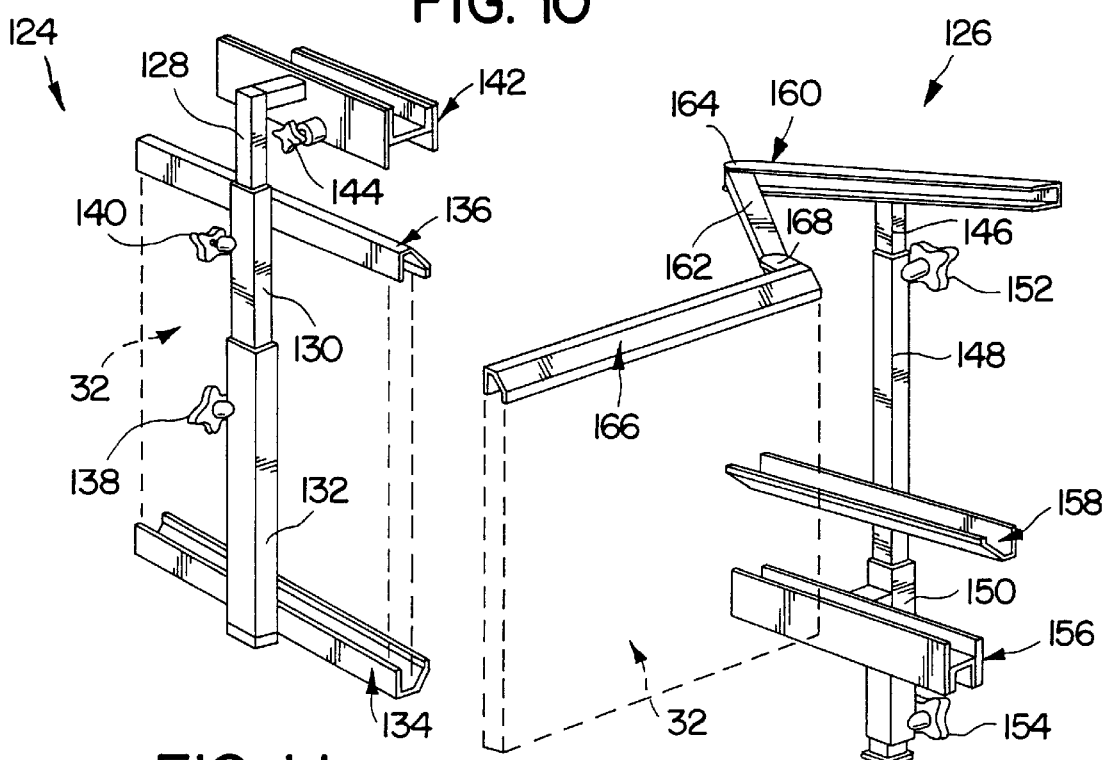
FIG. 11 is a perspective view illustrating details of the head section x-ray cassette holder of FIG. 10.
FIG. 12 is a perspective view illustrating further details of the side frame x-ray cassette holder of FIG. 10.

Other embodiments of cassette holders are illustrated in FIGS. 10–12. A removable head section cassette holder 124 is provided for positioning an x-ray cassette adjacent a bottom of deck 26. The cassette holder 124 is removable from the head section 90. An upright cassette holder 126 is also provided for attachment to side frame 16 of stretcher 10. Cassette holder 126 is useful for positioning an x-ray cassette adjacent to a patient lying on support surface 22.

Cassette holder 124 is best illustrated in FIG. 11. Cassette holder 124 includes first, second, and third telescoping members 128, 130, and 132, respectively. A lower cassette holding channel 134 is rigidly coupled to outer telescoping member 132. A top cassette holding channel 136 is rigidly coupled to telescoping member 130. A locking member 138 is rotatable to lock and release relative movement of telescoping members 130 and 132. Locking member 140 is provided to lock and release relative movement between telescoping members 128 and 130. A mounting channel 142 is coupled to inner telescoping member 128. The mounting channel 142 is configured to be positioned over a frame of the stretcher 10 as illustrated in FIG. 10. A locking member 144 can be adjusted to move a threaded retention member into engagement with the frame of the stretcher 10 to hold the cassette holder 124 on the stretcher 10.

A cassette 32 is positioned between first and second channels 134 and 136 as illustrated by the dotted lines in 10 and 11. The distance between channels 134 and 136 is adjusted by releasing locking member 138 and sliding telescoping members 130 and 134 relative to each other. After the cassette 32 is positioned within the channels 134 and 136, the locking member 138 is tightened. The position of the cassette 32 relative to the head section 90 is adjusted by releasing locking member 140 to permit sliding movement of the inner telescoping member 128 relative to telescoping member 130. Therefore, the channels 134 and 136 holding cassette 32 can be moved relative to deck 26 to align the cassette 32 at the desired location. Locking member 140 is then tightened.

Cassette holder 126 is further illustrated in FIG. 12. Cassette holder 126 includes first, second, and third telescoping members 146, 148, and 150, respectively. A first locking member 152 is provided between telescoping members 146 and 148. A second locking member 154 is provided between telescoping members 148 and 150. A mounting channel 156 is coupled to telescoping member 150. A bottom cassette retention channel 158 is rigidly coupled to center telescoping member 148. A support 160 is coupled to inner telescoping member 148. Support 160 is illustratively a U-shaped support. An arm 162 is pivotably coupled to one end of support 160 by a pivot connection 164. A cassette support channel 166 is pivotably coupled to an opposite end of arm 162 by pivot connection 168. After the mounting channel 156 is coupled to frame member 16 of stretcher 10, arm 162 and channel 166 can be pivoted outwardly to the position shown in FIG. 12 and in dotted lines in FIG. 10 to position an x-ray cassette 32 at a desired position over the patient support surface 22. For instance, if a patient is lying on his or her side, the x-ray cassette 32 can be held adjacent the patient's back using the outwardly pivoted arm and support channel 166 adjacent one end of the cassette 32. The other end of the cassette 32 is positioned against the support surface 22. The cassette holder 126 can also be used adjacent a side of patient support surface 22. If arm 162 and cassette channel 166 are pivoted inwardly toward support 160 as illustrated in FIG. 10, a cassette 32 may be positioned between support channels 158 and 166 adjacent the side of the support surface 22.

Mounting channels 142 and 156 are illustratively H-shaped channels. Therefore, the cassette holders 124 and 126 can each be mounted to either the head section or side section of the bed frame.

Figure 13:
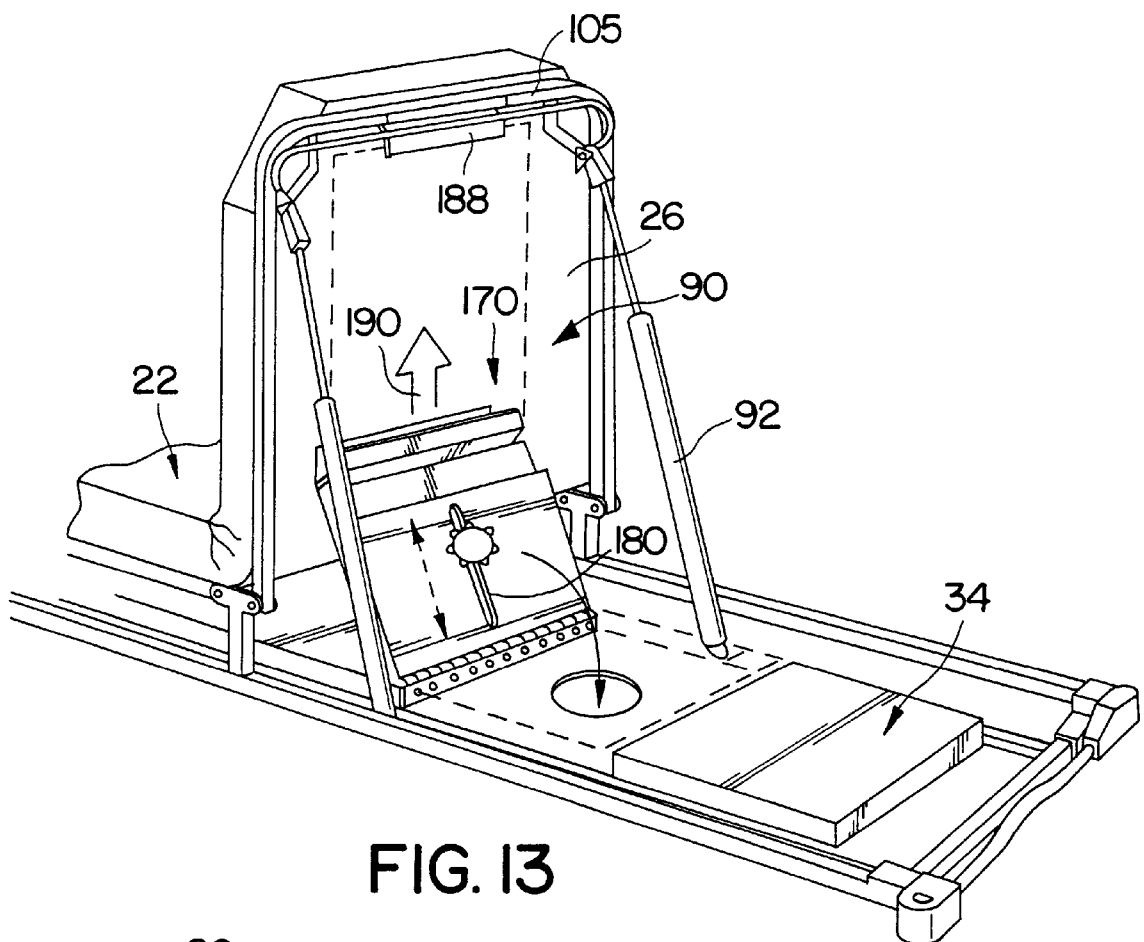
FIG. 13 is a perspective view illustrating another embodiment of an x-ray cassette holder for holding an x-ray cassette adjacent the bottom of the head section of the patient support surface when the head section is in the upwardly pivoted position.
Figure 14:
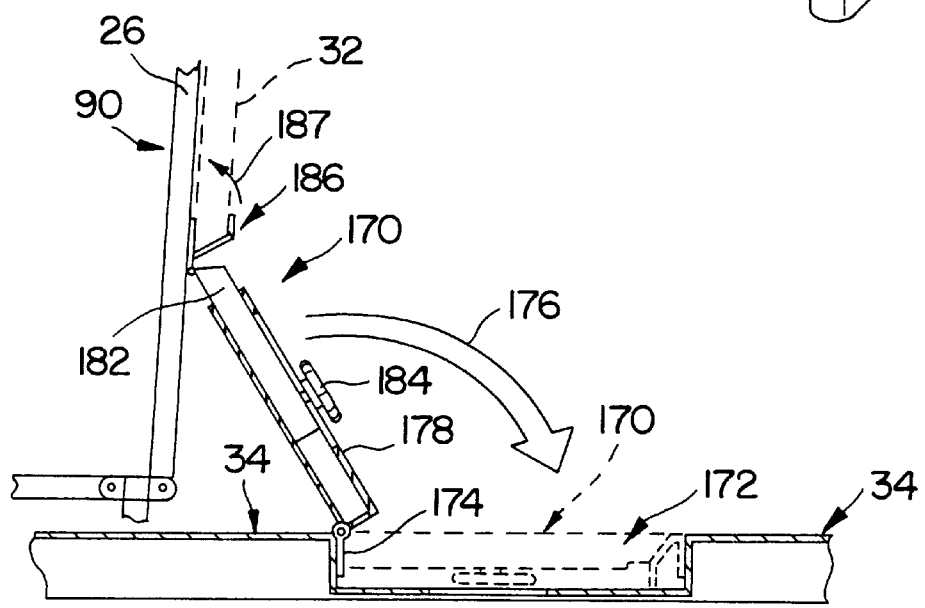
FIG. 14 is a partial sectional view illustrating further details of the cassette holder of FIG. 13.

Another embodiment of cassette holder is illustrated in FIGS. 13 and 14. In this embodiment, a cassette holder 170 is formed as a portion of x-ray tray 134. X-ray tray 34 is formed to include a recessed section 172. Cassette holder 170 is pivotably coupled to the x-ray tray 34 by hinge 174. When not in use, x-ray tray 170 is pivoted downwardly in the direction of arrow 176 of FIG. 14 to the dotted storage position. Cassette holder 170 includes a first member 178 which is coupled to hinge 174. Member 178 is formed to include a slot 180. An inner member 182 slides within an interior region of outer member 178. A locking mechanism 184 slides back and forth within slot 180. A cassette channel 186 is pivotably coupled to inner member 182 and spring biased toward the back section of deck 26 in the direction of arrow 187 to hold an end of a cassette 32 against the bottom of patient support deck 26. An upper cassette channel 188 is coupled to a top frame member 105 of stretcher 10.

During operation, cassette holder 170 is pivoted out of recess 172 to lie against the head section 90. Cassette 32 is loaded within channel 186. Inner member 182 is then extend upwardly in the direction of arrow 190 until a top end of cassette 32 engages top cassette channel 188. Locking mechanism 184 is then tightened to secure the inner member 182 relative to the outer member 178. This holds the cassette 32 against a bottom of deck 26. After the x-ray is taken, cassette holder 170 can be pivoted in the direction of arrow 176 to its storage position.

Figure 15:
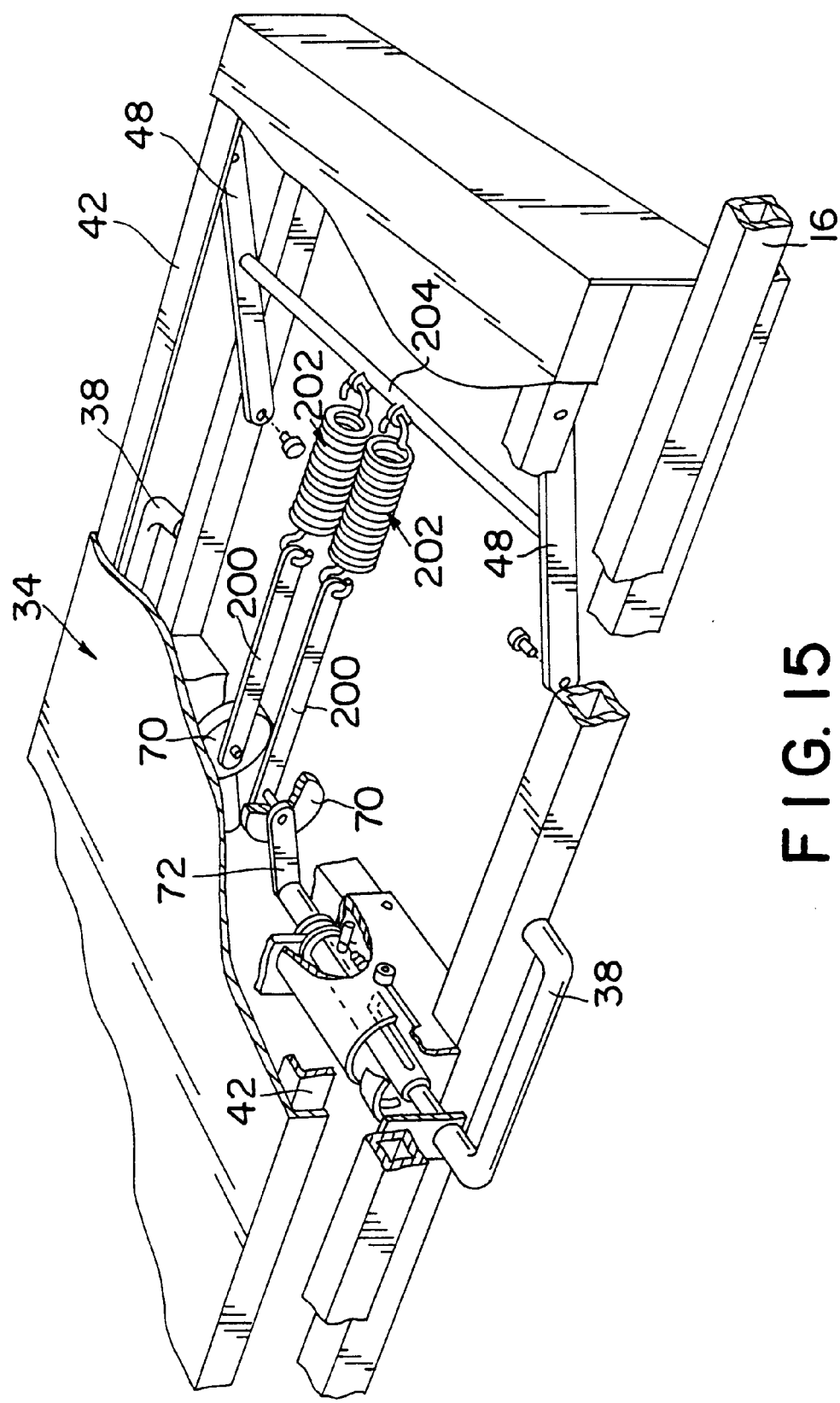
FIG. 15 is a partial perspective view, with portions broken away, illustrating details of a second embodiment of a lifting mechanism for moving the x-ray tray from its lowered cassette loading position to its elevated x-ray position.

Another embodiment of the lifting mechanism of the present invention is illustrated in FIGS. 15–17. Those elements referenced by numbers identical to FIGS. 5–7 perform the same or similar function. In the embodiment of FIGS. 15–17, handles 38 on opposite sides of the bed both rotate toward a foot end of the stretcher 10. As illustrated in FIG. 15, each of the rollers 70 is coupled to an arm 200. An opposite end of arm 200 is coupled to one end of spring 202. Another end of spring 202 is coupled to a cross bar 204 extending between members 48 of the parallelogram linkage 40.

Operation of the lifting mechanism is best illustrated in FIGS. 15 and 17. When the x-ray tray 34 is in its lowered position, slack exists between arms 200 and springs 202 to permit the x-ray tray to rest in its lowered loading position. As the handle 38 is rotated to move the rollers 70, spring 202 is extended as illustrated in the dotted lines of FIG. 16. As illustrated in FIG. 17, the roller 70 and arm 72 move over center so that the spring 202 holds the x-ray tray 34 in its upwardly extended position as illustrated in FIG. 17. Springs 202 are strong enough to hold the x-ray tray 34 and the cassette 32 against a bottom surface of deck 26. The lifting mechanism of FIGS. 15–17 accommodates x-ray cassettes 32 having different thicknesses.

Figure 18:
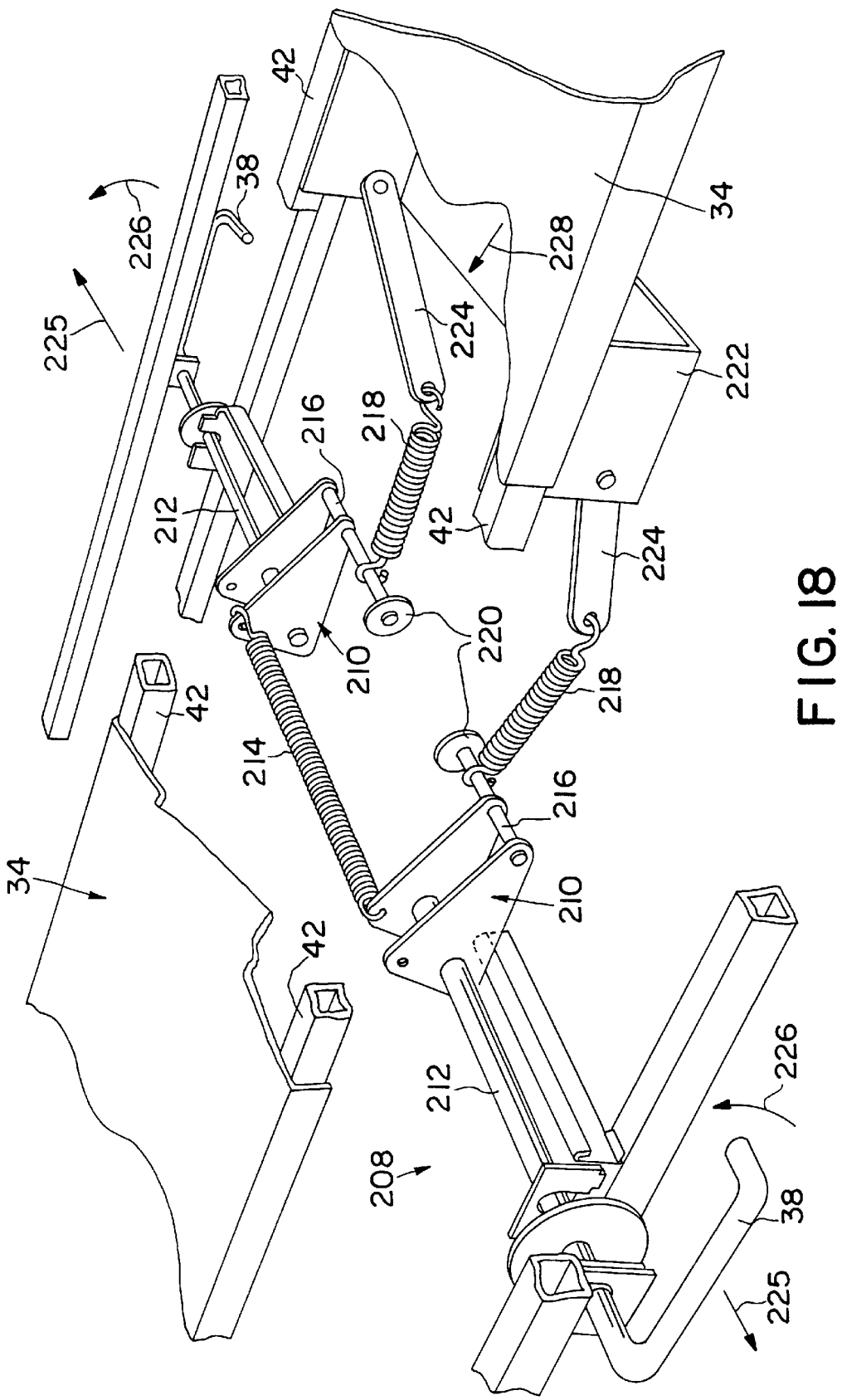
FIG. 18 is a sectional view of another lifting mechanism according to the present invention.

Still another embodiment of a lifting mechanism 208 is illustrated in FIG. 18. Those elements referenced by numbers identical to FIGS. 5–7 perform the same or similar function. In the embodiment of FIG. 18, handles 38 on opposite sides of the bed both rotate toward the foot end of stretcher 10. Handles 38 are coupled to triangular-shaped linkages 210 by shafts 212. A spring 214 connects the pair of linkages 210 to bias the handles 38 inwardly toward the center of the bed to a storage position. Lifting mechanism 208 further includes a pair of shafts 216 coupled to linkages 210.

First ends of springs 218 are coupled to shafts 216. Washers 220 on shafts 216 are provided to retain the springs 218 on the shafts 216. A support member 222 is rigidly coupled to frame members 42 of the parallelogram linkage.

Second ends of springs 218 are coupled to the support 222 by pivot connections 224.

When either handle 38 is extended outwardly in the direction of arrows 225 and then rotated in the direction of arrows 226, linkages 210 also rotate in the direction of arrows 226 to stretch the spring 218 on the side of the linkage 208 of the rotated handle 38. This causes the spring 218 to pull support 222 and the frame members 42 of the parallelogram linkage in the direction of arrow 228 which causes frame members 42 to slide relative to x-ray tray 34 as discussed above. This lifts the x-ray tray 34 to its elevated position beneath the patient support deck 26.

A further embodiment of the lifting mechanism 230 is illustrated in FIGS. 19–20. In this embodiment, the lifting mechanism 230 is slidable on lower frame members 44 in the direction of arrows 232 and 234. Handles 236 are provided to facilitate movement of the lifting mechanism 230. The x-ray tray 238 is located between side flanges 240 and 242 of cover 243 to maintain the horizontal position of x-ray tray 238 as the x-ray tray 238 is lifted upwardly in the direction of arrow 244 to the dotted position of FIG. 19. Lifting mechanism 230 includes a handle 246 on each side of the lifting mechanism 230. When one handle 246 is rotated in the direction of arrow 248. A parallel linkage 250 moves a support tray 252 upwardly to move the x-ray cassette 32 toward the patient support deck 26.

Figure 21:
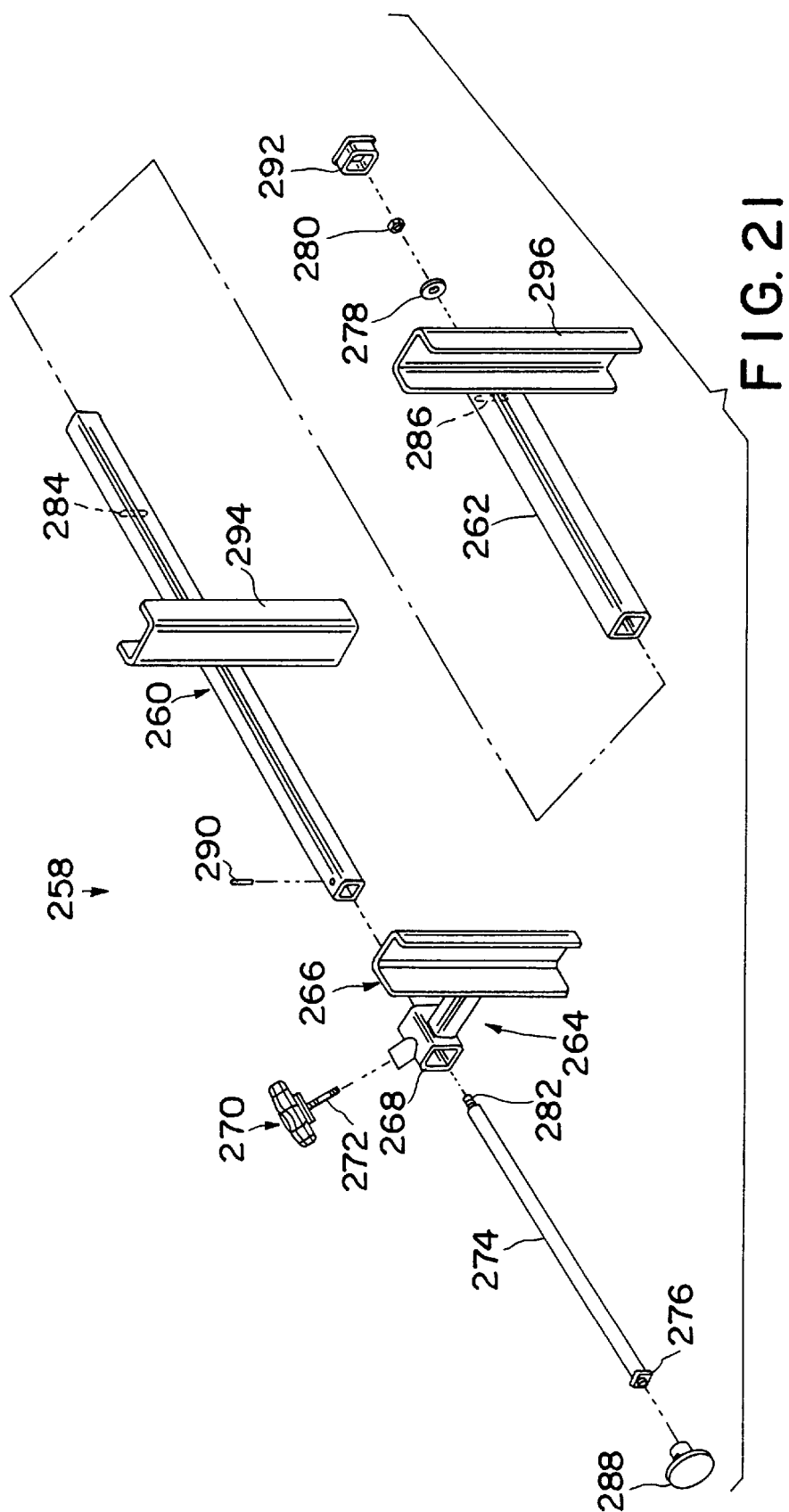
FIG. 21 is an exploded perspective view of another embodiment of an x-ray cassette holder of the present invention.

Another embodiment of cassette holder 258 is illustrated in FIG. 21. FIG. 21 includes two telescoping shafts 260 and 262. A mounting arm assembly 264 includes a U-shaped bracket 266 for mounting the holder 258 to a bed frame. A tube portion 268 slides over tube 260. A knob 270 includes a threaded shaft 272 to lock the mounting assembly 264 in position on tube 260. An extension rod 274 is located within tubes 260 and 262 to hold the tubes 260 and 262 together. Extension rod 274 has an end plate 276 welded to a first end. A washer 278 and nut 280 are coupled to an opposite threaded end 282 of extension rod 274. A pair of pins 284 and 286 extend through tube 260 and 262, respectively. Pins 284 and 286 are configured to engage washers 276 and 278, respectively, to hold tubes 260 and 262 together. A stop 288 is coupled to tube section 260 by pin 290. Stop 288 holds the mounting assembly 264 on the cassette holder 258. A top cap 292 is coupled to an end of tube 262.

In operation, the U-shaped member 266 is located on a frame of the bed. Tube sections 260 and 262 are then moved apart to load an x-ray cassette 32 between U-shaped channels 294 and 296. Top channel member 262 is then released and gravity moves the top tube 262 down over the tube 260 to retain the x-ray cassette 32 between the upper and lower channels 296 and 294.

Although the invention has been described in detail with reference to certain preferred embodiments, additional variations and modifications exist within the scope and spirit of the invention as described and defined in the following claims.

What is claimed is:

1. A bed comprising:
   a frame;
   a patient support deck coupled to the frame, the deck having a length dimension and a width dimension;
   an x-ray tray located below the deck and extending below substantially the entire length dimension of the deck, the x-ray tray being configured to receive an x-ray cassette; and
   a lifting mechanism located between the frame and the x-ray tray to move the x-ray tray from a lower first position spaced apart from the deck to permit loading of the x-ray cassette on the x-ray tray and an elevated second position located closer to the deck.

2. The bed of claim 1, wherein the x-ray tray moves only vertically relative to the frame between the lower first position and the elevated second position.

3. The bed of claim 2, wherein the lifting mechanism includes a linkage which slides relative to the x-ray tray so that the x-ray tray moves upwardly without horizontal movement relative to the frame.

4. The bed of claim 3, wherein the x-ray tray includes flanges at opposite ends which are configured to engage first and second cross members of the frame to hold the x-ray tray in the same horizontal position relative to the frame during movement of the x-ray tray.

5. The bed of claim 1, wherein the x-ray tray includes an upper x-ray cassette supporting surface and the lifting mechanism includes a parallelogram linkage coupled to the frame.

6. The bed of claim 1, wherein the x-ray tray includes a non-slip top surface for engaging the x-ray cassette.

7. The bed of claim 1, wherein the lifting mechanism includes a handle pivotably coupled to the frame and a wheel coupled to the handle, the wheel being configured to engage the x-ray tray and move the x-ray tray upwardly to its second elevated position when the handle is rotated relative to the frame.

8. A bed comprising:
   a frame;
   a patient support deck coupled to the frame;
   an x-ray tray located below the deck, the x-ray tray being configured to receive an x-ray cassette; and
   a lifting, mechanism located between the frame and the x-ray tray to move the x-ray tray from a lower first position spaced apart from the deck to permit loading of the x-ray cassette on the x-ray tray and an elevated second position located closer to the deck, the lifting mechanism including a handle pivotably coupled to the frame, the handle being movable to a storage position located under the frame.

9. The bed of claim 8, wherein the handle is spring-biased to the storage position.

10. The bed of claim 8, wherein the x-ray tray and the lifting mechanism are slidable on the frame below the patient support deck.

11. The bed of claim 8, wherein the x-ray tray moves only vertically relative to the frame between the lower first position and the elevated second position.

12. The bed of claim 11, wherein the lifting mechanism includes a linkage which slides relative to the x-ray tray so that the x-ray tray moves upwardly without horizontal movement relative to the frame.

13. The bed of claim 12, wherein the x-ray tray includes flanges at opposite ends which are configured to engage first and second cross members of the frame to hold the x-ray tray in the same horizontal position relative to the frame during movement of the x-ray tray.

14. The bed of claim 8, wherein the deck has a length dimension and a width dimension, and the x-ray tray extends below substantially the entire deck.

15. The bed of claim 8, wherein the x-ray tray includes an upper x-ray cassette supporting surface and the lifting mechanism includes a parallelogram linkage coupled to the frame.

16. The bed of claim 8, wherein the x-ray tray includes a non-slip top surface for engaging the x-ray cassette.

17. A bed comprising:

a frame;

a patient support deck coupled to the frame the deck having a bottom surface;

an x-ray tray located below the deck, the x-ray tray being configured to receive an x-ray cassette; and a lifting mechanism located between the frame and the x-ray tray to move the x-ray tray from a lower first position spaced apart from the deck to permit loading of the x-ray cassette on the x-ray tray and an elevated second position located closer to the deck, the lifting mechanism including a handle pivotably coupled to the frame; and a spring coupled between the handle and a linkage of the lifting mechanism, the spring being configured to hold the x-ray tray in its elevated second position to hold the x-ray cassette against the bottom surface of the deck regardless of a thickness of the x-ray cassette.

18. The bed of claim 17, wherein the x-ray tray moves only vertically relative to the frame between the lower first position and the elevated second position.

19. The bed of claim 18, wherein the lifting mechanism includes a linkage which slides relative to the x-ray tray so that the x-ray tray moves upwardly without horizontal movement relative to the frame.

20. The bed of claim 19, wherein the x-ray tray includes flanges at opposite ends which are configured to engage first and second cross members of the frame to hold the x-ray tray in the same horizontal position relative to the frame during movement of the x-ray tray.

21. The bed of claim 17, wherein the deck has a length dimension and a width dimension, and the x-ray tray extends below substantially the entire deck.

22. The bed of claim 17, wherein the x-ray tray includes an upper x-ray cassette supporting surface and the lifting mechanism includes a parallelogram linkage coupled to the frame.

23. The bed of claim 17, wherein the x-ray tray includes a non-slip top surface for engaging the x-ray cassette.

24. The bed of claim 17, wherein the handle is movable to a storage position located under the frame.

25. The bed of claim 24, wherein the handle is spring-biased to the storage position.

26. The bed of claim 25, wherein the x-ray tray moves only vertically relative to the frame between the lower first position and the elevated second position.

27. A bed comprising:

a frame;

a patient support deck coupled to the frame;

an x-ray tray located below the deck, the x-ray tray being configured to receive an x-ray cassette; and a lifting mechanism located between the frame and the x-ray tray to move the x-ray tray from a lower first position spaced apart from the deck to permit loading of the x-ray cassette on the x-ray tray and an elevated second position located closer to the deck, the lifting mechanism including a handle pivotably coupled to the frame and a spring having a first end coupled to the handle, a second end of the spring being coupled to a linkage of the lifting mechanism to lift the linkage and move the x-ray tray upwardly to its second elevated position when the handle is rotated relative to the frame.

28. The bed of claim 27, wherein the handle is movable to a storage position located under the frame.

29. The bed of claim 28, wherein the handle is spring-biased to the storage position.

30. The bed of claim 26, wherein the lifting mechanism includes a linkage which slides relative to the x-ray tray so that the x-ray tray moves upwardly without horizontal movement relative to the frame.

31. The bed of claim 30, wherein the x-ray tray includes flanges at opposite ends which are configured to engage first and second cross members of the frame to hold the x-ray tray in the same horizontal position relative to the frame during movement of the x-ray tray.

32. The bed of claim 27, wherein the deck has a length dimension and a width dimension, and the x-ray tray extends below substantially the entire deck.

33. The bed of claim 27, wherein the x-ray tray includes an upper x-ray cassette supporting surface and the lifting mechanism includes a parallelogram linkage coupled to the frame.

34. The bed of claim 27, wherein the x-ray tray includes a non-slip top surface for engaging the x-ray cassette.

* * * * *